United States Patent [19]
Patton

[11] 4,089,207
[45] May 16, 1978

[54] ACCESSORY FOR GAS CONCENTRATOR-GAS CHROMATOGRAPH ANALYZER

[75] Inventor: Jesse C. Patton, Lewisburg, W. Va.

[73] Assignee: The Bendix Corporation, Southfield, Mich.

[21] Appl. No.: 702,635

[22] Filed: Jul. 6, 1976

Related U.S. Application Data

[63] Continuation of Ser. No. 534,593, Dec. 20, 1975, abandoned.

[51] Int. Cl.² ............................................. G01N 31/08
[52] U.S. Cl. ................................ 73/23.1; 73/421.5 R
[58] Field of Search ................... 73/23, 23.1, 421.5 R, 73/422 GC; 23/232 R, 232 C, 254 R; 219/535

[56] References Cited

U.S. PATENT DOCUMENTS

| | | | |
|---|---|---|---|
| 2,489,654 | 11/1949 | Main-Smith et al. | 73/421.5 R |
| 3,093,001 | 6/1963 | Williams | 73/421.5 R |
| 3,363,447 | 1/1968 | Severs | 73/23.1 |
| 3,714,421 | 1/1973 | Josias et al. | 73/23.1 |
| 3,731,539 | 5/1973 | Brittan et al. | 73/421.5 R |
| 3,948,602 | 4/1976 | Solomon | 23/232 C |

*Primary Examiner*—Richard C. Queisser
*Assistant Examiner*—Stephen A. Kreitman
*Attorney, Agent, or Firm*—Bruce L. Lamb; William G. Christoforo

[57] ABSTRACT

An accessory for a gas concentrator-gas chromatograph system including a split heater block hinged to expose a channel shaped to receive a concentrator column. Quick detachable gas connections are aligned with the block channel facilitating rapid and convenient handling of concentrator columns when a number of similar analyses are to be conducted.

3 Claims, 8 Drawing Figures

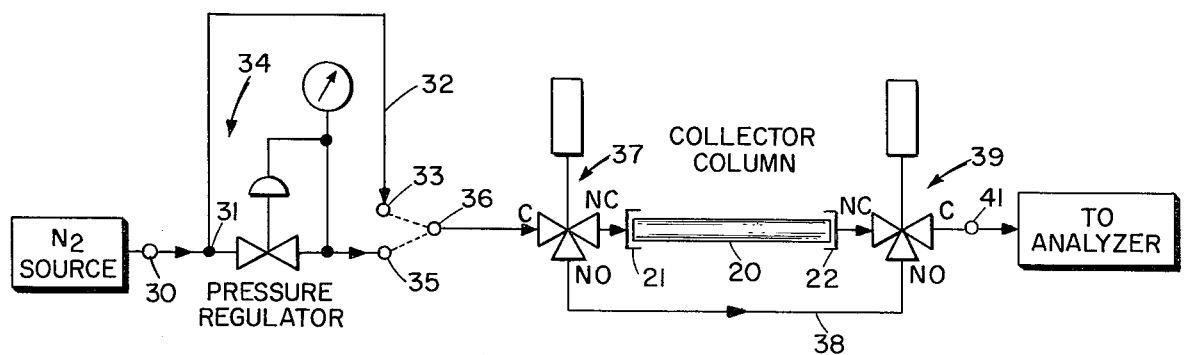
FIG. 6
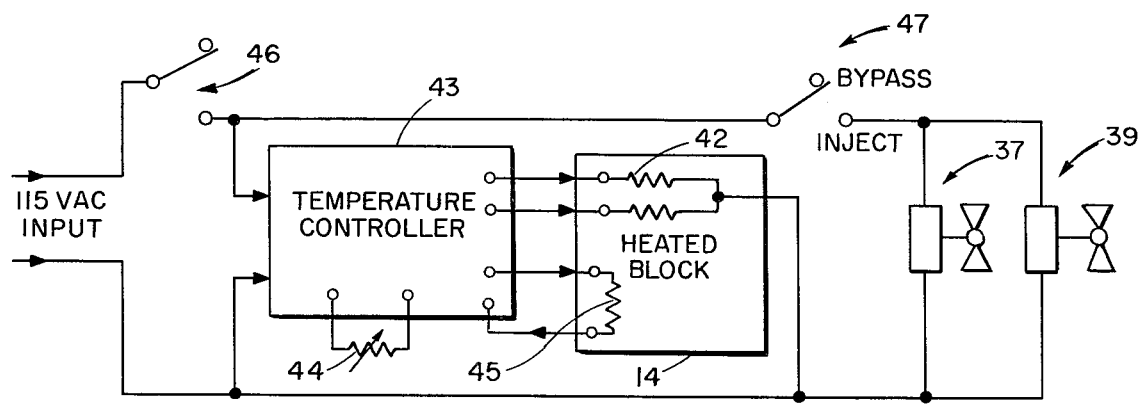
FIG. 7
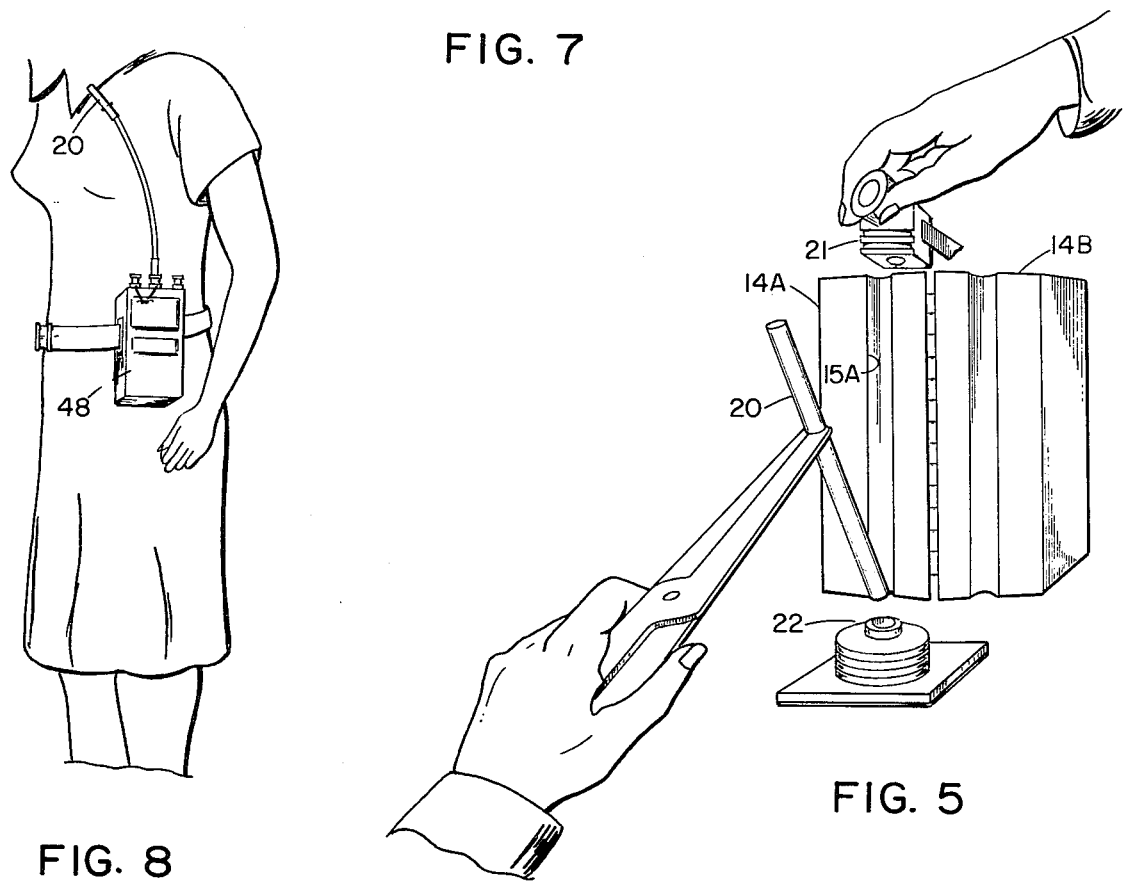
FIG. 8
FIG. 5

ACCESSORY FOR GAS CONCENTRATOR-GAS CHROMATOGRAPH ANALYZER

This application is a continuation of application Ser. No. 534,593, filed Dec. 20, 1974, now abandoned.

The present invention relates broadly to gas concentrating systems and more particularly to an accessory for a gas chromatograph to facilitate determination of the extent of exposure of personnel to potentially harmful vapors.

The recent identification of vinyl chloride as a carcinogen and the lowering of permissible limits of exposure have dramatized the need for methods and apparatus for monitoring industrial atmosphere to protect the health of workers who, in the course of their duties and, without their knowledge, may be breathing air contaminated by intolerable concentrations of gases of vapors. The monitoring method must be sensitive and selective. Preferably, it can be performed with a minimum or manipulative steps and will promptly yield results. The method approaching closest to the ideal at present involves gas chromatography together with a gas concentration step to provide adequate sensitivity. Other methods have required complex, time consuming analytical extractions which can be performed only by a skilled chemist under closely controlled conditions. On the other hand, a gas chromatograph designed for the detection of a particular analyte can be satisfactorily operated by persons of ordinary skill without specialized training and will produce results at a rate limited only by the elution time required for analyses, provided the apparatus is arranged for efficient use.

It is therefore an object of the present invention to provide a gas concentrator-gas chromatograph analytical system requiring only simple, rapidly performed manipulative steps and in which the possibility of contaminating the sample or creating other errors is very much reduced.

The invention is applied in a monitoring system of one form in which each individual whose degree of exposure to a particular gas or vapor is to be determined is provided with sampling apparatus to be worn on the person during periods of possible exposure. The sampling apparatus comprises a portable vacuum pump to which is attached a collector column consisting of a relatively short length of glass or metal tubing containing a packing material capable of adsorbing and retaining the analyte vapor. At the end of the sampling period the collector column is removed from the vacuum pump, one end of the column is connected to a carrier gas source, the other end of the column is connected to the inlet of a gas chromatograph and the column is then rapidly heated to volatize the retained analyte, whereupon the inlet to the chromatograph is opened and carrier gas is applied to the collector column to sweep the sample into the analytical column of the chromatograph. The output signal from the chromatograph detector is usually presented in chart form from which the operator determines the area of the signal peak occurring at the known elution time of the analyte and thus its quantity. From the quantity, the known flow rate and the sample time of the vacuum pump, the concentration of analyte vapor to which the individual has been exposed is readily calculated.

Briefly, the present invention comprises a flasher assembly in which the above described steps of connecting the collector column to the carrier gas source and chromatograph inlet and heating the column are facilitated by providing an oven-like housing containing a heater block and gas coupling joints for each end of the collector column. The heater block contains a central bore corresponding to the outside diameter of the collector column; is split along the axis of the bore and is linked to a door of the housing so that upon opening the housing door the block is laid open to expose a semi-cylindrical, column receiving channel. The gas coupling joints are positioned above and below the block along the axis of the bore therein. One of the joints is pivotally mounted and each includes a resilient sealing member to provide a gas tight seal to the collector column when the latter is slipped into place in the heater block channel.

In the drawings:

FIG. 5 illustrates insertion or removal of a collector column in the flasher;

FIGS. 6 and 7 are schematic diagrams of the gas flow and electrical controls of the invention; and FIG. 8 illustrates one manner of collecting samples in a column.

Figure 2:
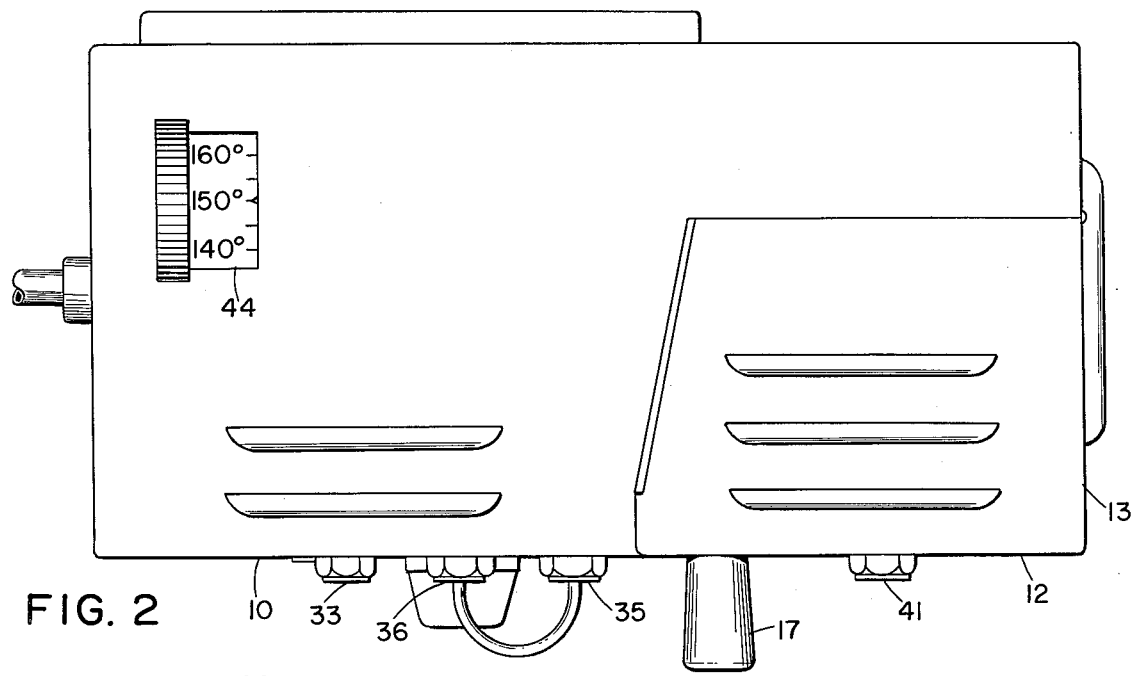
FIGS. 1 and 2 are exterior elevation and plan views of the invention.
Figure 1:
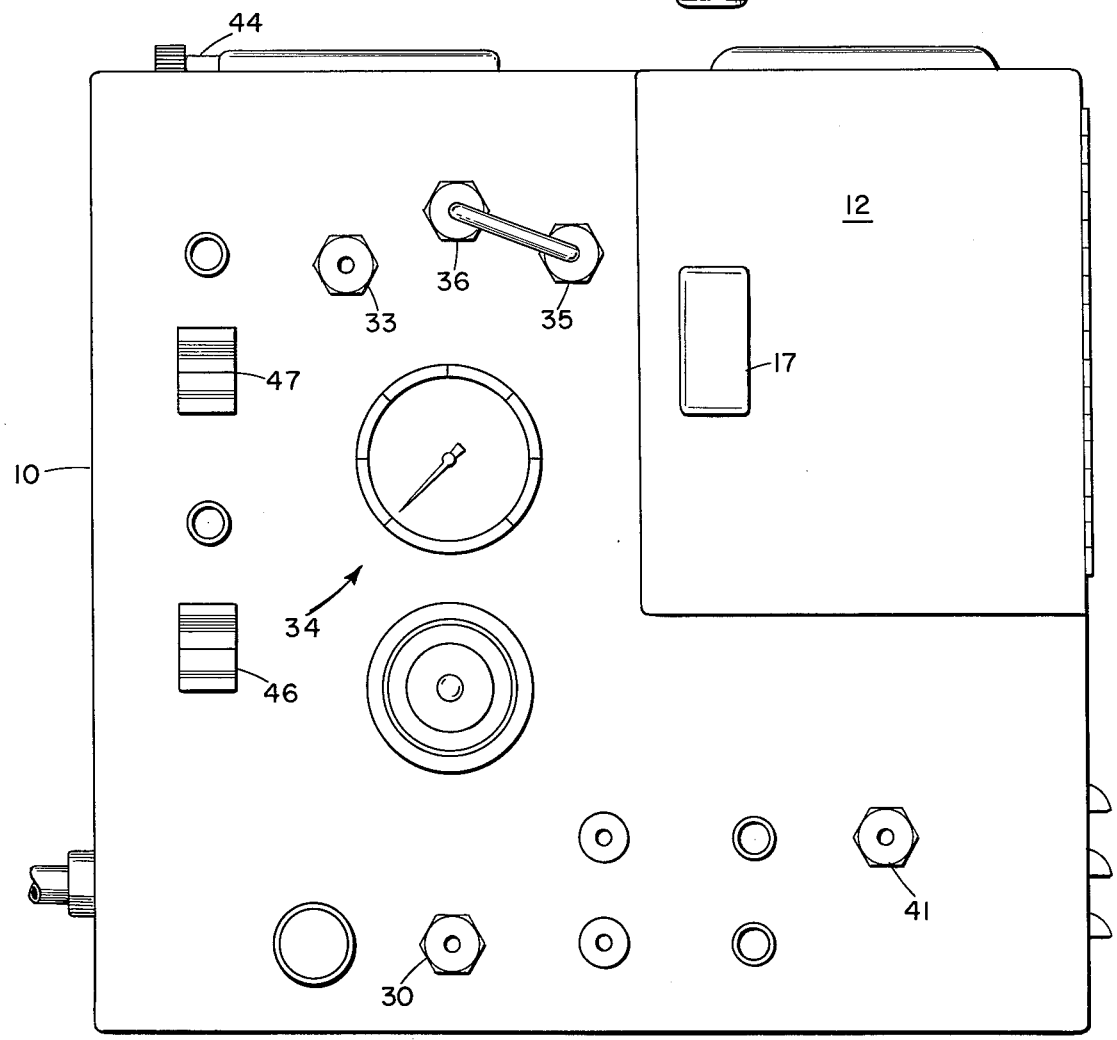
Figure 4:
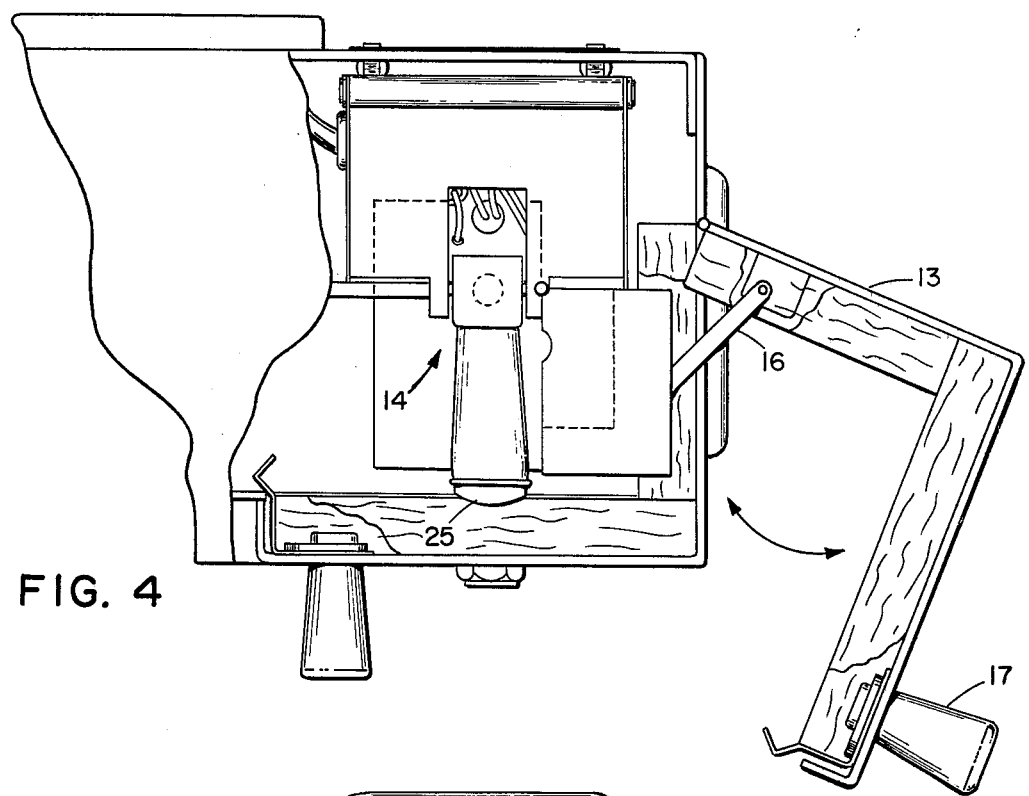
FIGS. 3 and 4 are fragmented elevation and plan views with portions thereof broken away to show details of the invention.
Figure 3:
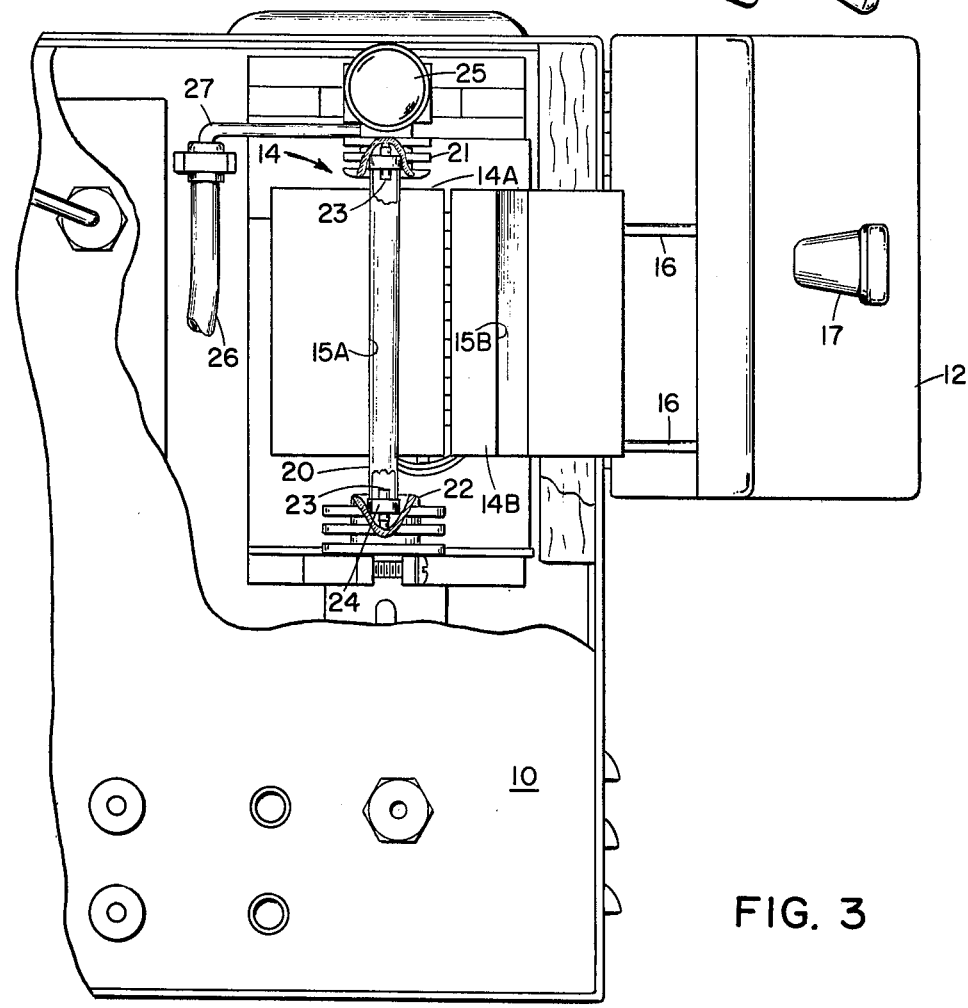

Referring to FIGS. 1–4 of the drawings, the flasher assembly is contained within an outer housing 10 (FIG. 1) which also encloses valving, temperature and operating controls later to be described. A generally L-shaped door 12 which is hinged along a downwardly extending panel 13 cut from the end wall of housing 10 is openable to expose and simultaneously lay open a collector column heater block 14, as shown in FIGS. 3 and 4. Block 14 is composed of two half-portions 14a, 14b hinged together along one edge, each of which is provided with a semi-cylindrical channel 15a, 15b which, when block halves 14a and 14b are brought into facing relationship, define a cylindrical bore dimensioned to snugly surround a collector column. Both block halves 14a, 14b are provided with cartridge-type electrical heaters (not shown) and one or both halves are provided with a temperature sensor, such as a platinum wire thermometer (not shown). The outer surfaces of block halves 14a and 14b are surrounded by suitable heat insulating material.

Block half 14a is fixed in housing 10. Block half 14b, hinged to block half 14a, is connected through swing links 16 to door 12. Opening door 12 by means of external handle 17 swings block 14b into the open position shown in FIGS. 3 and 4.

Referring particularly to FIG. 3, a collector column 20 is shown positioned in channel 15a of block half 14a. Aligned with the axis of column 20 and channel 15a are a socket-like gas inlet connection 21 and a socket-like gas outlet connection 22. Each of these connections include a nipple portion 23 extending a short distance into the bore of column 20 and a resilient sealing ring 24 abutting the end edge of column 20. Inlet connection 21 is attached to a pivotally mounted handle 25, best seen in FIG. 4. Gas is supplied to connection 21 from a source through a portion 26 of flexible tubing connected to a portion 27 of rigid conduit leading into nipple 23. When handle 25 is lifted upwardly, connection 21 clears the upper end of column 20 during the course of which column 20 is tilted slightly forwardly from channel 15a facilitating lifting the column from the channel and from the outlet connector 22. When a collector column is to be inserted in the flasher assembly the lower end of the column 20 is slipped into outlet connector 22 and the column is pushed nearly upright into position in channel 15a. Handle 21 is then lowered to bring the inlet connector 21 into position over the upper end of column 20 to carry the column into final alignment in channel 15a and provide a gas tight seal at both the upper and lower ends of the column. FIG. 5 illustrates an operation which could be either the initial stage of installing a collector column in the flasher assembly or the final stage of removing a column from the assembly.

FIGS. 6 and 7 illustrate schematically the gas flow and electrical controls contained within housing 10. Referring to FIG. 6, carrier gas from a source such as a nitrogen cylinder is supplied to connector 30, whence it is conducted through Tee fitting 31 and bypass loop 32 to connector 33 or through pressure regulator 34 to connector 35. If the gas source is pressure regulated, pressure regulator 34 is not required and the gas flows through Tee 31 and loop 32 to connector 33, whence it is conducted by a tubular jumper to connector 36, while connector 35 is plugged. If the gas source is not pressure regulated, connector 33 is plugged and the jumper is installed between connectors 35 and 36. From connector 36 the gas is conducted to the common port of a solenoid controlled switching valve 37. The normally open port of valve 37 is connected through a bypass loop 38 to the normally open port of a second solenoid controlled switching valve 39 and from the common port thereof to an outlet connector 41, whence it is conducted to the inlet of a gas chromatograph analyzer. After the collector column has been installed in the flasher assembly a sufficient amount of time for the column contents to be vaporized, valves 37 and 39 are energized, whereupon the normally open valve ports are closed and the normally closed valve ports are opened. Bypass 38 is then blocked off and the vaporized contents of the column are swept from the column to the analyzer input by carrier gas flow through connector 21, column 20 and connector 22.

Referring to FIG. 7, the electrical heating elements 42 of block 14 receive power from a temperature controller 43 of known design. Controller 43 includes an adjustable temperature selector 44 and a block temperature sensor 45. Power is supplied to controller 43 through an SPST On-Off switch 46 and from switch 46 through an SPST switch 47 to the solenoids of valves 37 and 39.

FIG. 8 shows one manner of collecting a sample in column 20. The column is attached to the person, preferably in the vicinity of the face. One end of the column is connected through flexible tubing to the inlet of a battery operated pump 48, also worn on the person. Air at breathing level is drawn through column 20 by pump 48 at a calibrated rate. The pump may run continuously or at programmed intervals, depending upon the substance being monitored, tolerable limits of exposure and other conditions. At the conclusion of a work shift or such other time as may be appropriate, column 20 is detached from the pump tubing and the contents collected in the column may be analyzed as described above. Alternatively, columns and pumps may be located at fixed stations to provide representative samples of the atmosphere in a work area or other locale. The vapors collected by the column are retained therein and columns may be stored at room temperature for a considerable time before analysis without significant loss of the collected vapor in amounts likely to cause appreciable error in later analysis.

The invention claimed is:

1. A flasher assembly for use in a gas concentrator-gas chromatograph analytical system wherein the concentrator includes a column packed with adsorbent material, comprising a housing having a hinged door therein;

a thermally conductive heater block having a substantial heat capacity mounted within said housing and accessible upon opening said door, said block having a channel therein to receive the concentrator column in thermally conductive contact and being divided into two hinged together relatively movable to expose said block channel;

means linking said housing door to one of said block parts so that opening said door moves said one block part into a position exposing said block channel;

an inlet gas conduit for supplying carrier gas to said concentrator column and an outlet gas conduit for conveying gas and vapors from said concentrator column to the inlet of the gas chromatograph;

a socket-like connector for each of said inlet and outlet conduit, said connectors being positioned at opposite ends of said block channel and in alignment therewith, and being adapted to slidingly receive the ends of said concentrator column and provide a gas tight connection thereto, one of said connectors being fixedly mounted with respect to said block, the other of said connectors being movably mounted with respect to said block to provide clearance permitting the sliding engagement of disengagement of said concentrator column with said connectors.

2. A flasher as claimed in claim 1 with additionally, valve means for each said inlet and outlet conduits, and a bypass conduit interconnecting said valve means, said valve means being operable to direct carrier gas flow through said concentrator column or to divert carrier gas flow around said column.

3. A flasher as claimed in claim 1 wherein said movably mounted connector is pivotally mounted to move in an arc directed away from said block channel.

* * * * *